United States Patent [19]

Brandt et al.

[11] Patent Number: 4,863,491

[45] Date of Patent: Sep. 5, 1989

[54] INTERFACE FOR LIQUID CHROMATOGRAPHY-MASS SPECTROMETRY SYSTEMS

[75] Inventors: Rune Brandt, St.-Heddinge, Denmark; Robert Nordman, Palo Alto, Calif.

[73] Assignee: Hewlett-Packard, Palo Alto, Calif.

[21] Appl. No.: 199,554

[22] Filed: May 27, 1988

[51] Int. Cl.$^4$ .................... B01D 45/04; B01D 15/08
[52] U.S. Cl. ............................... 55/15; 55/17; 55/277; 210/198.2; 250/288
[58] Field of Search ............... 55/15, 17, 257.1, 277, 55/261; 250/281, 282, 288, 288 A; 210/656, 198.2

[56] References Cited

U.S. PATENT DOCUMENTS

| | | | |
|---|---|---|---|
| 3,616,596 | 11/1971 | Campargue | 55/17 |
| 3,725,271 | 4/1973 | Giannotti | 55/17 X |
| 3,912,470 | 10/1975 | Fluckiger | 55/17 X |
| 3,957,470 | 5/1976 | Dawes | 55/17 X |
| 4,112,297 | 9/1978 | Miyagi et al. | 250/288 A |
| 4,160,161 | 7/1979 | Horton | 250/288 A |
| 4,286,153 | 8/1981 | Janner et al. | 55/17 X |
| 4,298,795 | 11/1981 | Takeuchi et al. | 250/288 A |
| 4,358,302 | 11/1982 | Dahneke | 55/17 X |
| 4,383,171 | 5/1983 | Sinha et al. | 250/288 A |
| 4,531,056 | 7/1985 | Labowsky et al. | 250/288 A |
| 4,629,478 | 12/1986 | Browner et al. | 55/257.1 |
| 4,769,540 | 9/1988 | Mitsui et al. | 250/288 |

FOREIGN PATENT DOCUMENTS

624264 7/1961 Canada .................... 55/15

*Primary Examiner*—Robert Spitzer
*Attorney, Agent, or Firm*—Robert P. Sabath

[57] ABSTRACT

A particle separation for use as an interface between a liquid chromatograph and a mass spectrometer comprises a vacuum chamber, an inlet nozzle for the chamber, a conical skimmer, and a vacuum exhaust port. The nozzle admits a stream of gas containing desolvated particles into a vacuum chamber as a supersonic jet. Heavier particles tend to concentrate near the central axis of the jet with lighter gas and vapor further from the axis. On entering the vacuum chamber, the jet forms a standing barrel shock wave extending from the nozzle to an aperture in the apex of the skimmer. The exterior angle formed by the conical surface of the skimmer is set so that the standing barrel shock wave attaches to the conical surface. The distance between the nozzle and the aperture is selected so that the skimmer pierces the downstream Mach disk of the shock wave so that the central particle beam enters the aperture without being perturbed by the mach disk. A vacuum exhaust port is disposed downstream from the skimmer aperture to allow gas flowing along the surface of the skimmer to be evacuated with minimal resistance. A multistage particle beam separator comprises all the elements of a single stage particle beam separator and, in addition, a second vacuum chamber, second conical surfaced skimmer, second skimmer aperture, and second vacuum exhaust port.

9 Claims, 3 Drawing Sheets

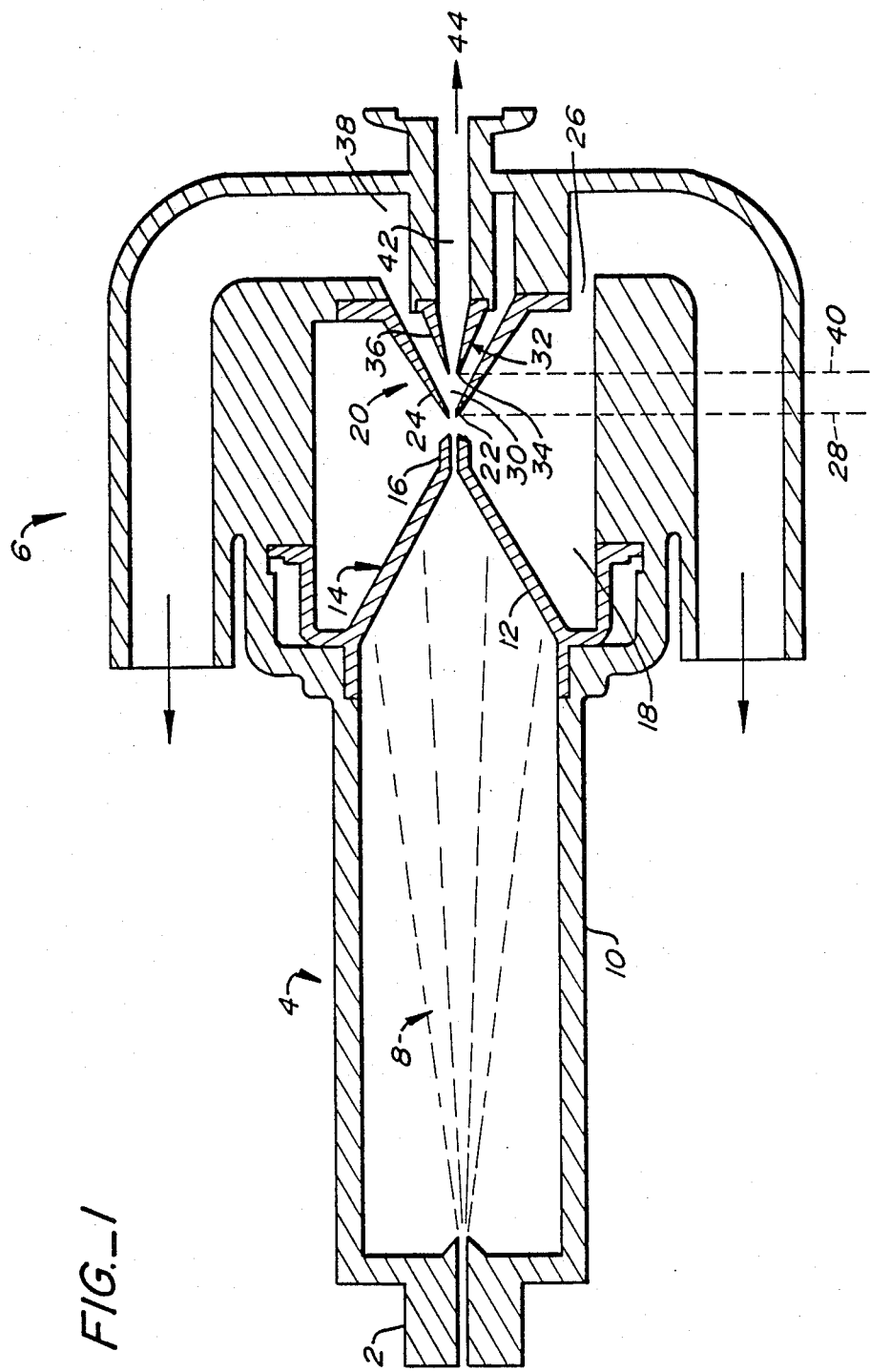
FIG._1

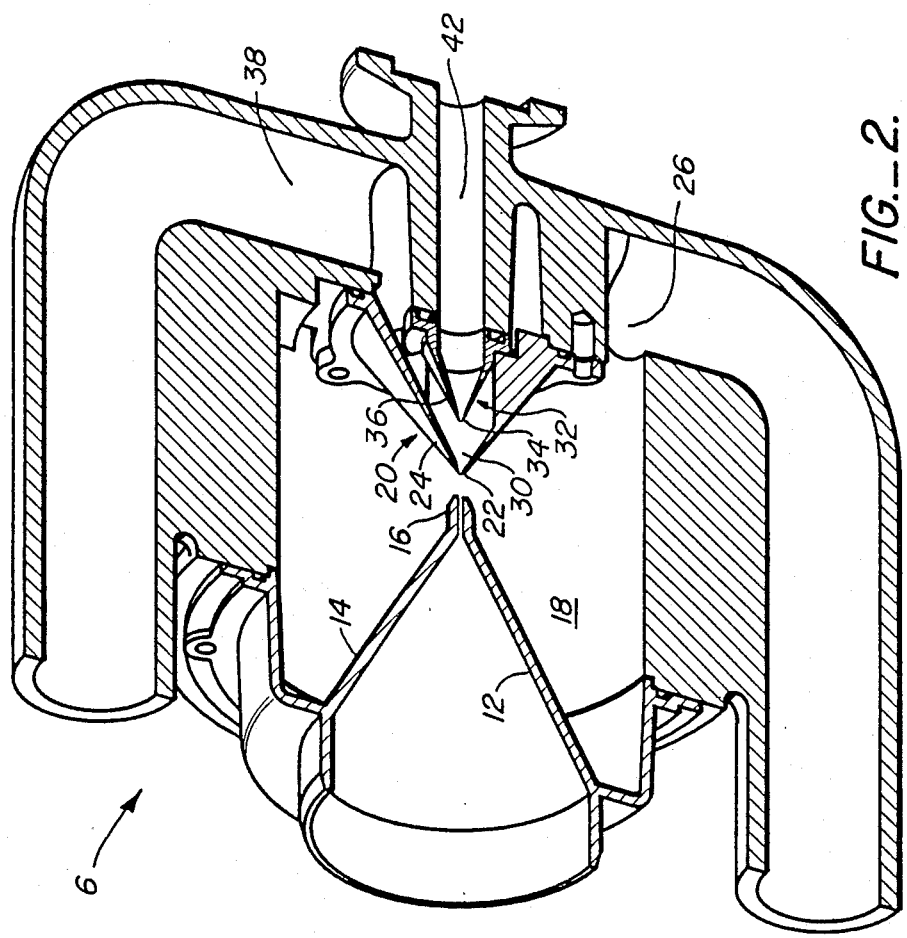
FIG._2.

FIG._3
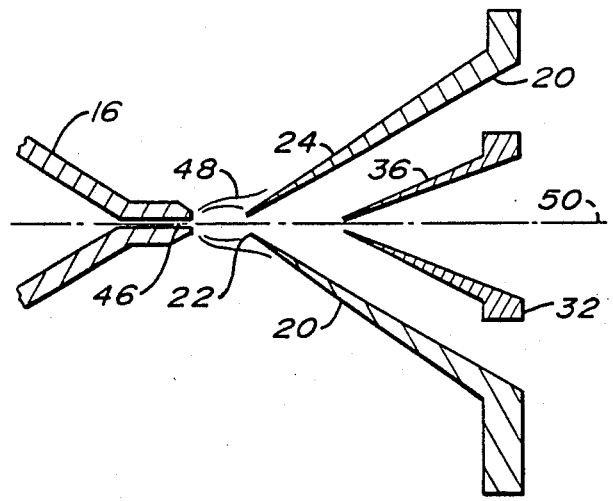
FIG._4
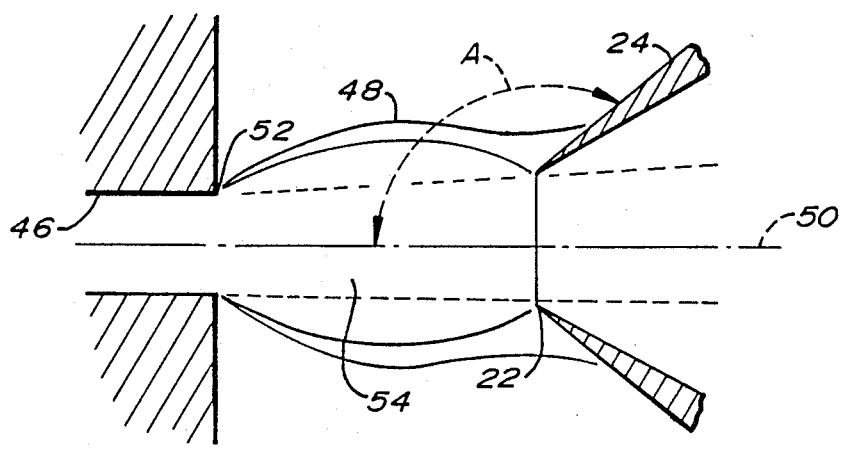

INTERFACE FOR LIQUID CHROMATOGRAPHY-MASS SPECTROMETRY SYSTEMS

FIELD OF THE INVENTION

This invention relates to an interface for separating desolvated particles from a stream of gas which is particularly suitable for use in combined liquid chromatography-mass spectrometry systems and in supercritical fluid chromatography-mass spectrometry systems. In particular, this invention is directed to a staged particle beam separator which separates a beam of desolvated particles from solvent vapor and other gases in one or more successive vacuum chamber stages. In one application of this separator, the nebulized, desolvated effluent of a liquid chromatography column, containing entrained desolvated particles, is passed through one or more successive vacuum chambers wherein the entrained desolvated particles are skimmed from the gas stream, and the particles stream obtained is passed to the ion source of a mass spectrometry system.

BACKGROUND OF THE INVENTION

The coupling of mass spectrometers with liquid chromatography systems has provided a very valuable tool for identifying organic compounds. The unique value of the liquid chromatographic separation systems is their ability to separate solutions containing mixtures of organic compounds into liquid fractions containing individual compounds. However, the product of the liquid chromatographic column is an eluant liquid solution of the compound or compounds to be analyzed at atmospheric pressure. The mass spectrometer analyzes compounds in a high vacuum system. Evaporation of the eluant solvent and presentation of the desolvated particles to the ionization chamber of the mass spectrometer in a suitable form for ionization has presented serious difficulties limiting the sensitivity of the mass spectrometer and greatly complicating its efficient operation. The high vacuum required in the ionization chamber cannot be achieved in the presence of a significant quantity of residual solvent liquid. Therefore, efficient solvent separation and isolation of the desolvated particles are critical for optimum mass spectrometry operation.

The early systems relied upon the vacuum expansion to reduce the relative proportions of non-volatile component to solvent component passed to the ion chamber. U.S. Pat. No. 3,997,298 describes a system wherein eluant liquid is injected from a capillary tube into a vacuum chamber, and the gaseous products are passed directly to the ion chamber. In a similar approach, the system described in U.S. Pat. No. 4,647,772 atomizes a liquid sample in a vacuum chamber, and the gaseous products are passed through an aperture opening leading to the ionization chamber; the conical aperture has an axis perpendicular to the direction of flow of gases through the vacuum chamber. U.S. Pat. No. 4,730,111 and Vestal, M. International Journal of Mass Spectrometry and Ion Physics. 46:193-196 describe similar systems wherein heat is supplied to assist in the evaporation of the solvent. The amount of solvent passed to the ion chamber by these systems is undesirably high for most effective operation of the mass spectrometer.

DESCRIPTION OF THE PRIOR ART

U.S. Pat. No. 4,112,297 describes an interface for a liquid chromatograph and mass spectrometer comprising an ultrasonic nebulizer, expansion chamber and a cooler where evaporated solvent is condensed and removed from the gas stream.

U.S. Pat. No. 4,298,795 (FIG. 4) describes a system for preparing liquid samples for mass spectroscopy comprising a capillary nebulizer (1) for converting the liquid input to a spray of particles in a vacuum chamber (9). The particle spray is collected in a tapered inlet of a transfer tube (24) and fed into a second vacuum chamber or concentration chamber (23) through a capillary tube. An introduction tube (13) leading to the ion chamber has an opening axially aligned with and opposing the outlet of the capillary tube (24). The inlet end of the introduction tube (13) has a conical face. The vacuum exhaust ports leading to the pumps (12, 25) are positioned perpendicular to the capillary outlets in the vacuum chambers. In this system, particles are separated from the solvent gases by skimming.

U.S. Pat. No. 4,629,478 describes a monodisperse aerosol generator comprising a nebulizer and a two stage vacuum system for evaporating solvent and separating the desolvated particles formed from the solvent vapor and other gases. In FIG. 1, the nozzle end 32 of the tube 26 leading into the first chamber 28 is precisely aligned with the flat inlet end 33 of the tube 34 forming a first skimmer. The separation between 33 and 34 is about 1-3 cm. Similarly, the nozzle end 35 is aligned with the flat inlet end 36 of the tube 37 leading to the mass spectrometer M and spaced from 1-3 cm therefrom to form a second skimmer.

The THERMABEAM TM system (Extrel Corporation, Pittsburgh, PA) comprises a thermal nebulizer and expansion chamber wherein nebulization and desolvation is effected. It also includes a two-stage particle beam separator which leads to the ion source of the mass spectrometer. Based on information provided by the company, this two stage system appears to be similar to the system in U.S. Pat. No. 4,629,478.

The entire contents of U.S. Pat. Nos. 4,298,795 and 4,629,478 are hereby incorporated by reference in their entireties.

SUMMARY AND OBJECTS OF THE INVENTION

In summary, the apparatus of this invention comprises an interface which is particularly suitable for liquid chromatograph-mass spectrometers and for supercritical fluid chromatograph-mass spectrometers. The interface can be a single or multiple stage particle beam separator. The primary separator comprises a vacuum chamber having a capillary inlet tube, a skimmer having a particle outlet opening axially aligned with the central axis of the capillary inlet tube and opposed thereto, and a vacuum exhaust port. The capillary inlet tube has a constant inner diameter of from 0.1 to 1.0 mm and preferably from 0.2 to 0.8 mm and a terminal length which is at least from about 3 to 4 times the inner diameter thereof. The skimmer has a conical surface concentric with the central axis of the particle outlet opening, the conical surface forming an angle of from about 145° to 160° with the central axis of the particle outlet opening. The 145° to 160° angle relative to the central axis corresponds to a 40° to 70° exterior angle of the skimmer. The particle outlet opening is spaced from 1 to 15 mm and preferably from 1 to 8 mm from the opposed end of the capillary inlet tube. The vacuum exhaust port is preferably axially downstream in the direction of gas and particle flow behind a plane perpendicular to the flow axis and extending through the particle outlet opening. A second particle beam separator comprising a second conical surfaced skimmer in a vacuum chamber is preferably provided as a second stage separator.

The method of this invention for separating particles from a gas stream in a vacuum chamber comprises passing a stream of gas containing particles to be separated into the vacuum chamber through a capillary inlet opening at a supersonic speed to form a standing barrel shock wave extending from the capillary inlet to the surface of a skimmer, the skimmer having an axially concentric outlet opening opposed to the inlet opening. The standing barrel shock wave maintains a beam of particles axially concentric therewith and passing out of the vacuum chamber through the outlet opening. The outlet opening extends through the Mach disk to within the shock wave and is thus unobstructed thereby. Preferably, the skimmer has a conical face forming an angle with the axis of the outlet opening which maintains the standing barrel shock wave.

It is an object of this invention to provide a more efficient and reliable separation of desolvated particles from nebulized and desolvated effluent streams of a liquid chromatograph.

It is a further object of this invention to provide a higher yield of desolvated particles suspended in a gas containing a smaller proportion of eluant solvent vapors from liquid chromatographic eluants for mass spectrometry analysis.

It is a still further object of this invention to provide a separation of desolvated particles in a separation chamber with stabilized gas and particle flow patterns which permits the use of larger nozzle sizes, reducing clogging tendencies of the orifices, and producing less solid buildup on the surfaces.

BRIEF DESCRIPTION OF THE DRAWINGS

FIG. 1 is a cross-sectional view of the particle beam interface of this invention.

FIG. 2 is a cross-sectional isometric view of the particle beam separator of this invention.

FIG. 3 is a schematic view of the nozzle and skimmers of this invention.

FIG. 4 is a schematic view of the standing barrel shock wave and its relationship to the stage 1 skimmer.

DETAILED DESCRIPTION OF THE INVENTION

The particle beam interface of this invention is designed to prepare a liquid sample containing a solute to be analyzed for mass spectrometric analysis. The liquid must be atomized, solvent evaporated, and a high yield of desolvated particles directed to the ionization chamber of the mass spectrometer (MS). This procedure is particularly valuable for, but is not limited to, the treatment of the eluants from liquid chromatographic columns.

Referring to FIG. 1, a cross-sectional view of the particle beam interface of this invention is shown. This system comprises a nebulizer 2 where the liquid solution is broken into droplets, desolvation chamber 4 where the solvent is evaporated, leaving particles which might contain traces of residual solvent, and momentum separator 6 where the particles are further desolvated and separated from solvent vapors, in preparation for ionization.

The nebulizer 2 projects a stream of solvent droplets 8 into a cylindrical chamber 10 which has a pressure of about 100 to 400 torr and a temperature of from about 25 to 60° C. Here the solvent is evaporated, leaving an aerosol or suspension of particles containing a small proportion of residual solvent. The actual preferred pressure and temperature is application dependent and is adjusted depending upon the solute being analyzed and the solvent of the input stream.

FIG. 2 is an isometric, cross-sectional view of the particle beam separator shown in FIG. 1 and can be viewed in conjunction therewith. The mixture of solvent vapors, gases and desolvated particles is collected by the tapered collector side 12 of the nozzle plate 14 and, by means of the pressure drop across the nozzle, is projected through the nozzle as a supersonic jet. The higher mass particles tend to concentrate near the center of the axis of the jet with the lower mass gas molecules further from the axis, thus forming a particle beam. This particle beam travels into and through the first stage chamber 18 of the momentum separator 6 where the solvent vapors and other gases are removed from the mixture. As described in greater detail hereinafter with respect to FIG. 3 and FIG. 4, the particle beam exists within an envelope of shock waves commonly referred to as a barrel shock wave, of which the downstream transverse face is commonly referred to as the Mach disc. The first stage skimmer 20 has a central ax opening 22 which samples the particle beam. It also has an axially concentric conical surface 24 which penetrates the Mach disk and has a critical angle such that the flow of gases along the conical surface is attached.

The gases from the first stage chamber 18 are removed through the first exhaust port 26. To promote the stability of the standing shock wave and particle beam, exhaust port 26 is located downstream in the direction of gas flow behind a plane 28 which is perpendicular to the axis of the first skimmer and which passes through the entrance of the axial opening 22.

The gas and particle mixture is passed through a series of chambers in the momentum separator of this invention, each chamber having a stronger vacuum than the preceeding chamber. The term "downstream", as used herein, is defined to mean the direction of material flow from weaker vacuum to stronger vacuum. This exhaust port placement in the momentum separator section is an improvement over the prior art skimmers which have the exhaust ports placed in front of the plane or in the plane through the skimmer opening. The position of the exhaust port 26 increases the efficiency of gas removal through the port and prevents formation of a high pressure pocket, thus supporting the uniform movement of the gas in the direction of the exhaust port as it is deflected by the conical surface 24.

The particle beam then enters into the second stage chamber 30 which has a further reduced pressure of about 0.5 torr where the gases are further expanded and separated from the particles. The particles continue to travel in a beam configuration which continues through the axial, central opening 34 of a second skimmer 32. The gases are deflected by the conical surface 36 of the second skimmer 32 toward the second vacuum exhaust port 38. The second exhaust port 38 is positioned downstream in the direction of gas and particle movement behind a plane 40 perpendicular to the axis of the second skimmer and passing through the entrance of the axial opening 34. The position of the exhaust port 38 behind the plane 40 further promotes the gas flow patterns in the second vacuum chamber 30 and the integrity of the particle beam.

The particles passing through the axial opening 34 of the second skimmer 32 are carried through the outlet passageway 42 to the ionization chamber 44 (not shown) of the mass spectrometer.

A schematic view of the nozzle and skimmers of this invention is shown in FIG. 3. The trajectories of the individual particles are aligned or collimated into a parallel trajectory column or particle beam in passing through passageway 46 of the nozzle 16. To achieve the collimation, the central collimating passageway 46 should have an inner diameter of from 0.1 to 1.0 mm and preferably from 0.2 to 0.8 mm. It should have a minimum length of from about 3 to 4 times the diameter thereof. The optimum dimensions are selected depending upon the characteristics of the solvent composition. A passageway length significantly greater than about 4 times the passageway diameter increases resistance to gas flow therethrough with no significant advantage, since a greater length does not significantly increase the collimation.

The gas stream passes out of the passageway 46 at a supersonic speed, forming a barrel shaped shock wave 48 shown in greater detail in FIG. 4. The first stage skimmer 20 has a conical surface 24 which forms an angle A of from about 145° to 160° with the central axis 50 of the skimmer. Angle A cooperates with the nozzle to support a standing barrel shock wave extending from the tip 52 of the nozzle 46 to the first skimmer surface 24. The particles are concentrated by the barrel shock wave 48 in an axial particle beam 54. If angle A is less than about 145°, the shock wave may detach from the surface 24 and the Mach disk would then form a barrier across the entrance of opening 22, disrupting the particle beam, and causing a portion of the particles to be deflected to the vacuum exhaust system. If angle A is greater than about 160°, it may not be effective to capture or cause attachment of the shock wave to the surface of the skimmer.

The separation between the nozzle outlet 52 and the first skimmer inlet opening 22 should be from 1 to 15 mm and preferably from 1 to 8 mm to promote a stable barrel shock wave with most solvents.

The backside of the first skimmer 20 is preferably tapered to have a slightly larger angle than the conical surface 36 of the second skimmer 32 and thus to provide a maximum expansion volume in the second vacuum chamber.

The momentum particle beam separator of this invention provides more effective particle separation from gases. It also provides a separation of desolvated particles in a separation chamber with stabilized gas and particle flow patterns which permits the use of larger nozzle sizes, reducing clogging tendencies of the orifices, and producing less solid buildup on the skimmer surfaces.

The interface of this invention is particularly suitable for use as an interface between a liquid chromatograph or a supercritical fluid chromatograph and a mass spectrometer. It will be readily apparent, however, that it is useful for preparing any solution of a volatile solvent containing a non-volatile substance for MS analysis, and the invention is not limited to liquid chromatographic, supercritical fluid chromatographic or mass spectrometer systems.

We claim:

1. A method for separating particles from a gas stream in a vacuum chamber comprising passing said stream of gas containing particles to be separated into said vacuum chamber through a capillary inlet at a supersonic speed to form a standing barrel shock wave extending from said capillary inlet to the surface of a skimmer having an axially concentric outlet and to form a particle beam axially concentric therewith and passing out of said vacuum chamber through said outlet, said outlet extending through the Mach disk of said shock wave and being unobstructed thereby.

2. The method of claim 1 wherein said skimmer has a conical outer surface forming an angle between 40° and 70°.

3. A particle beam separator comprising:
   a first vacuum chamber;
   introduction means for introducing a time-varying mixture of gas and particles into said first vacuum chamber so as to define a supersonic jet therein, said supersonic jet forming a standing barrel shock wave having a Mach disk and a central axis, said particles forming a particle beam extending along said central axis and substantially confined to a radially inward cross section of said shock wave, said cross section taken orthogonally to said central axis;
   a first skimmer having a first conical surface which radially narrows to a first apex opposed to said introduction means, said first conical surface forming a first outer angle between 40° and 70° so that said shock wave attaches thereto, said first skimmer having a first aperture in said first apex, said first aperture being axially aligned with said central axis, said first apex being spaced so that said first skimmer pierces said Mach disk so that said particle beam exits said first vacuum chamber via said first aperture and so that most of said gas is diverted along said conical surface; and
   a first vacuum exhaust port.

4. The separator of claim 3 wherein said first skimmer defines a first plane through said first apex and orthogonal to said central axis, said first vacuum exhaust port being downstream of said first plane.

5. The separator of claim 4 further comprising:
   a second vacuum chamber downstream of and communicating with said first aperture; said
   a second skimmer having a second apex with a second aperture second aperture being coaxial with said central axis and in communication with said second vacuum chamber, said second skimmer being downstream of said second vacuum chamber so that said particle beam exits and second vacuum chamber via said second aperture and said gas is further separated from said particle beam; and
   a second vacuum exhaust port.

6. The separator of claim 5 wherein said second skimmer defines a second plane through said second apex and orthogonal to said central axis, said second vacuum exhaust port being downstream of said second plane.

7. The separator of claim 4 wherein said introduction means includes a capillary inlet tube.

8. The separator of claim 7 wherein said introduction means further includes:
   nebulizer means for dispersing into droplets a time-varying solution containing solvent and sample compounds to be analyzed; and
   desolvation means for evaporating said solvent from said droplets to provide that said sample compounds are largely desolvated, said desolvation means communicating with said nebulizer means.

9. A liquid chromatograph to mass spectrometer interface comprising:

nebulizer means for dispersing into droplets a time-varying solution containing solvent and sample compounds to be analyzed;

desolvation means for evaporating said solvent from said droplets so that said sample compounds are largely desolated, said desolvation means communicating with said nebulizer means;

a first vacuum chamber;

introduction means for introducing a time-varying mixture of gas and particles into said first vacuum chamber so as to define a supersonic jet therein, said supersonic jet forming a standing barrel shock wave having a central axis, said particles forming a particle beam extending along said central axis and substantially confined to a radially inward cross section of said shock wave, said cross section taken orthogonally to said central axis;

a first skimmer having a first conical surface which radially narrows to a first apex opposed to said introduction means, said first conical surface forming a first outer angle between 40° and 70° so that said shock wave attaches thereto, said first skimmer having a first aperture in said first apex, said first aperture being axially aligned with said central axis, said first skimmer defining a first plane through said first apex and orthogonal to said central axis said first apex being spaced so that said first skimmer pierces said Mach disk so that said particle beam exists said first vacuum chamber via said first aperture and so that most of said gas is diverted along said conical surface;

a first vacuum exhaust port downstream of said first plane;

a second vacuum chamber downstream of and communicating with said first aperture;

a second skimmer having a second apex with a second aperture, said second aperture being coaxial with said central axis and in communication with said second vacuum chamber, said second skimmer being downstream of said second vacuum chamber so that said particle beam exits said second vacuum chamber via said second aperture and said gas is further separated from said particle beam; and a second vacuum exhaust port.

* * * * *